(12) United States Patent
Haines

(10) Patent No.: US 8,287,545 B2
(45) Date of Patent: Oct. 16, 2012

(54) METHODS AND APPARATUS FOR ENHANCED RETENTION OF PROSTHETIC IMPLANTS

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 1652 days.

(21) Appl. No.: 11/075,836

(22) Filed: Mar. 8, 2005

(65) Prior Publication Data

US 2006/0030944 A1   Feb. 9, 2006

Related U.S. Application Data

(63) Continuation-in-part of application No. 11/036,584, filed on Jan. 14, 2005, which is a continuation-in-part of application No. 11/049,634, filed on Feb. 2, 2005, now abandoned.

(60) Provisional application No. 60/551,096, filed on Mar. 8, 2004, provisional application No. 60/551,080, filed on Mar. 8, 2004, provisional application No. 60/551,078, filed on Mar. 8, 2004, provisional application No. 60/551,631, filed on Mar. 8, 2004, provisional application No. 60/551,307, filed on Mar. 8, 2004, provisional application No. 60/551,262, filed on Mar. 8, 2004, provisional application No. 60/551,160, filed on Mar. 8, 2004, provisional application No. 60/536,320, filed on Jan. 14, 2004, provisional application No. 60/540,992, filed on Feb. 2, 2004.

(51) Int. Cl.
A61F 2/46   (2006.01)

(52) U.S. Cl. .................................. 606/86 R; 606/88
(58) Field of Classification Search .................. 606/64, 606/86 R, 88; 623/20.34
See application file for complete search history.

(56) References Cited

U.S. PATENT DOCUMENTS 2,697,433 A   12/1954   Zehnder
3,457,922 A   7/1969   Ray
(Continued)

FOREIGN PATENT DOCUMENTS

EP   0104732   4/1984
(Continued)

OTHER PUBLICATIONS

U.S. Appl. No. 11/036,584, Inventor: Haines, filed Jan. 14, 2005.
(Continued)

*Primary Examiner* — Nicholas Woodall
(74) *Attorney, Agent, or Firm* — Patterson Thuente Christensen Pedersen, P.A.

(57) ABSTRACT

A prosthetic implant utilizes lateral retaining structures as part of the interior surface of the implant to more effectively secure and retain the implant while reducing the overall size and mass of the implant. In one embodiment, the prosthetic implant is provided with one or more T-shaped members extending from the inner surface of the implant, with the cross-member of the T-shaped member forming the laterally retaining structure that mate with a correspondingly shaped channel formed in the bone and are inserted into that channel at one or more oversize locations along the channel. In another embodiment, the prosthetic implant is provided with one or more retentions apertures in a projection structure extending inwardly from the inner surface of the implant that are laterally secured with a force fitted cross pin inserted through the retention aperture.

18 Claims, 30 Drawing Sheets

U.S. PATENT DOCUMENTS

| | | |
|---|---|---|
| 3,739,662 A | 6/1973 | Windelman et al. |
| 3,748,662 A | 7/1973 | Helfet |
| 3,774,244 A | 11/1973 | Walker |
| 3,798,679 A | 3/1974 | Ewald |
| 3,816,855 A | 6/1974 | Salch |
| 3,906,550 A | 9/1975 | Rostoker |
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,000,525 A | 1/1977 | Klawitter |
| 4,016,606 A | 4/1977 | Murray |
| 4,069,824 A | 1/1978 | Weinstock |
| 4,178,641 A | 12/1979 | Grundel |
| 4,207,627 A | 6/1980 | Cloutier |
| 4,213,209 A | 7/1980 | Insall |
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Petersen |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundei |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,808,185 A | 2/1989 | Penenberg |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,963,153 A * | 10/1990 | Noesberger et al. ........ 623/20.32 |
| 4,971,075 A | 11/1990 | Lee |
| 4,979,949 A | 12/1990 | Matsen |
| 4,986,833 A * | 1/1991 | Worland .................... 623/19.11 |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr |
| 5,080,675 A | 1/1992 | Lawes |
| 5,092,869 A | 3/1992 | Waldron |
| 5,098,436 A | 3/1992 | Ferrante |
| 5,100,409 A | 3/1992 | Coates |
| 5,108,398 A * | 4/1992 | McQueen et al. ............... 606/62 |
| 5,112,336 A | 5/1992 | Krevolin |
| 5,116,375 A | 5/1992 | Hofmann |
| 5,122,144 A | 6/1992 | Bert |
| 5,129,909 A | 7/1992 | Sutherland |
| 5,133,758 A | 7/1992 | Hollister |
| 5,133,759 A | 7/1992 | Turner |
| 5,137,536 A * | 8/1992 | Koshino .................... 623/20.34 |
| 5,147,364 A | 9/1992 | Comparetto |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,263,956 A | 11/1993 | Nobles |
| 5,269,786 A | 12/1993 | Morgan |
| 5,275,603 A | 1/1994 | Ferrante |
| 5,279,575 A | 1/1994 | Sugarbaker |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Peterson |
| 5,358,527 A | 10/1994 | Forte |
| 5,358,529 A | 10/1994 | Davidson |
| 5,358,531 A | 10/1994 | Goodfellow |
| 5,364,401 A | 11/1994 | Ferrante |
| 5,364,402 A | 11/1994 | Mumme |
| 5,370,699 A | 12/1994 | Hood |
| 5,370,701 A | 12/1994 | Finn |
| 5,391,170 A | 2/1995 | McGuire |
| 5,397,330 A | 3/1995 | Mikhail |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson, Jr. |
| 5,443,464 A | 8/1995 | Russell |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellow |
| 5,514,136 A | 5/1996 | Richelsoph |
| 5,514,139 A | 5/1996 | Goldstein |

| | | | | | | |
|---|---|---|---|---|---|---|
| 5,514,143 A | 5/1996 | Bonutti | | 6,195,577 B1 | 2/2001 | Truwit |
| 5,520,694 A | 5/1996 | Dance | | 6,197,064 B1 | 3/2001 | Haines |
| 5,520,695 A | 5/1996 | Luckman | | 6,203,576 B1 | 3/2001 | Afriat |
| 5,540,695 A | 7/1996 | Levy | | 6,206,926 B1 | 3/2001 | Pappas |
| 5,542,947 A | 8/1996 | Treacy | | 6,210,443 B1 | 4/2001 | Marceaux |
| 5,549,683 A * | 8/1996 | Bonutti ............... 623/20.33 | | 6,235,060 B1 | 5/2001 | Meesenburg |
| 5,549,684 A | 8/1996 | Amino | | 6,236,875 B1 | 5/2001 | Bucholz |
| 5,549,688 A | 8/1996 | Ries | | 6,264,697 B1 | 7/2001 | Walker |
| 5,551,429 A | 9/1996 | Fitzpatrick | | 6,285,902 B1 | 9/2001 | Kienzle |
| 5,562,674 A | 10/1996 | Stalcup | | 6,306,146 B1 | 10/2001 | Dinkler |
| 5,569,262 A | 10/1996 | Carney | | 6,306,172 B1 | 10/2001 | O'Neil |
| 5,571,100 A | 11/1996 | Goble | | 6,325,828 B1 | 12/2001 | Dennis |
| 5,578,039 A | 11/1996 | Vendrely | | 6,340,363 B1 | 1/2002 | Bolger |
| 5,593,411 A | 1/1997 | Stalcup | | 6,342,075 B1 | 1/2002 | MacArthur |
| 5,597,379 A | 1/1997 | Haines | | 6,348,058 B1 | 2/2002 | Melkent |
| 5,601,563 A | 2/1997 | Burke | | 6,361,564 B1 | 3/2002 | Marceaux |
| 5,601,566 A | 2/1997 | Dance | | 6,368,353 B1 | 4/2002 | Arcand |
| 5,609,645 A | 3/1997 | Vinciguerra | | 6,375,658 B1 | 4/2002 | Hangody |
| 5,611,802 A | 3/1997 | Samuelson | | 6,379,388 B1 | 4/2002 | Ensign |
| 5,613,969 A | 3/1997 | Jenkins, Jr. | | 6,401,346 B1 | 6/2002 | Roberts |
| 5,628,749 A | 5/1997 | Vendrely | | 6,406,497 B2 | 6/2002 | Takei |
| 5,639,279 A | 6/1997 | Burkinshaw | | 6,413,279 B1 | 7/2002 | Metzger |
| 5,643,272 A | 7/1997 | Haines | | 6,430,434 B1 | 8/2002 | Mittelstadt |
| 5,643,402 A | 7/1997 | Schmid | | 6,436,145 B1 | 8/2002 | Miller |
| 5,649,928 A | 7/1997 | Grundei | | 6,443,991 B1 | 9/2002 | Running |
| 5,653,714 A | 8/1997 | Dietz | | 6,458,128 B1 | 10/2002 | Schulze |
| 5,658,293 A | 8/1997 | Vanlaningham | | 6,470,207 B1 | 10/2002 | Simon |
| 5,667,511 A | 9/1997 | Vendrely | | 6,475,241 B2 | 11/2002 | Pappas |
| 5,681,354 A | 10/1997 | Eckhoff | | 6,477,400 B1 | 11/2002 | Barrick |
| 5,682,886 A | 11/1997 | Delp | | 6,482,409 B1 | 11/2002 | Lobb |
| 5,690,632 A | 11/1997 | Schwartz | | 6,485,519 B2 | 11/2002 | Meyers |
| 5,690,635 A | 11/1997 | Matsen, III | | 6,491,699 B1 | 12/2002 | Henderson |
| 5,690,637 A | 11/1997 | Wen | | 6,491,726 B2 | 12/2002 | Pappas |
| 5,697,935 A | 12/1997 | Moran | | 6,500,208 B1 | 12/2002 | Metzger |
| 5,702,458 A | 12/1997 | Burstein | | 6,506,215 B1 | 1/2003 | Letot |
| 5,723,016 A | 3/1998 | Minns | | 6,520,964 B2 | 2/2003 | Tallarida |
| 5,725,530 A | 3/1998 | Popken | | 6,554,838 B2 | 4/2003 | McGovern |
| 5,728,162 A | 3/1998 | Eckhoff | | 6,575,980 B1 | 6/2003 | Robie |
| 5,755,801 A | 5/1998 | Walker | | 6,579,290 B1 | 6/2003 | Hardcastle |
| 5,755,803 A | 5/1998 | Haines | | 6,595,997 B2 | 7/2003 | Axelson, Jr. et al. |
| 5,755,804 A | 5/1998 | Schmotzer | | 6,620,198 B2 | 9/2003 | Burstein |
| 5,766,257 A | 6/1998 | Goodman | | 6,623,526 B1 | 9/2003 | Lloyd |
| 5,769,855 A | 6/1998 | Bertin | | 6,645,251 B2 | 11/2003 | Salehi |
| 5,769,899 A | 6/1998 | Schwartz | | 6,672,224 B2 | 1/2004 | Weber |
| 5,776,200 A | 7/1998 | Johnson | | 6,679,917 B2 | 1/2004 | Ek |
| 5,782,921 A | 7/1998 | Colleran | | 6,685,711 B2 | 2/2004 | Axelson |
| 5,782,925 A | 7/1998 | Collaz | | 6,694,168 B2 | 2/2004 | Traxel |
| 5,799,055 A | 8/1998 | Peshkin | | 6,694,768 B2 | 2/2004 | Lu |
| 5,800,552 A | 9/1998 | Forte | | 6,695,848 B2 | 2/2004 | Haines |
| 5,810,827 A | 9/1998 | Haines | | 6,697,664 B2 | 2/2004 | Kienzle |
| 5,824,100 A | 10/1998 | Kester | | 6,697,768 B2 | 2/2004 | Jones et al. |
| 5,824,102 A | 10/1998 | Buscayret | | 6,701,174 B1 | 3/2004 | Krause |
| 5,824,105 A | 10/1998 | Ries | | 6,702,821 B1 | 3/2004 | Bonutti |
| 5,871,545 A | 2/1999 | Goodfellow | | 6,711,432 B1 | 3/2004 | Krause et al. |
| 5,871,546 A | 2/1999 | Colleran | | 6,725,080 B2 | 4/2004 | Melkent |
| 5,879,354 A | 3/1999 | Haines | | 6,755,563 B2 | 6/2004 | Wahlig |
| 5,879,392 A | 3/1999 | McMinn | | 6,755,835 B2 * | 6/2004 | Schultheiss et al. .......... 606/304 |
| 5,906,643 A | 5/1999 | Walker | | 6,755,864 B2 | 6/2004 | Brack |
| 5,908,424 A | 6/1999 | Bertin | | 6,764,516 B2 | 7/2004 | Pappas |
| 5,925,049 A | 7/1999 | Gustilo | | 6,770,097 B2 | 8/2004 | Leclercq |
| 5,935,173 A | 8/1999 | Roger | | 6,773,461 B2 | 8/2004 | Meyers |
| 5,944,758 A * | 8/1999 | Mansat et al. ............. 623/19.14 | | 6,783,550 B2 | 8/2004 | MacArthur |
| 5,954,770 A | 9/1999 | Schmotzer | | 6,796,988 B2 | 9/2004 | Melkent et al. |
| 5,980,526 A | 11/1999 | Johnson | | 6,827,723 B2 | 12/2004 | Carson |
| 5,986,169 A | 11/1999 | Gjunter | | 6,858,032 B2 | 2/2005 | Chow |
| 5,997,577 A | 12/1999 | Herrington | | 6,875,222 B2 | 4/2005 | Long |
| 6,039,764 A | 3/2000 | Pottenger | | 6,886,684 B2 | 5/2005 | Hacikyan |
| 6,056,754 A | 5/2000 | Haines | | 6,898,858 B1 | 5/2005 | Spell |
| 6,059,788 A | 5/2000 | Katz | | 6,911,044 B2 | 6/2005 | Fell |
| 6,068,658 A | 5/2000 | Insall | | 6,916,324 B2 | 7/2005 | Sanford |
| 6,080,195 A | 6/2000 | Colleran | | 6,916,340 B2 | 7/2005 | Metzger |
| 6,083,228 A | 7/2000 | Michelson | | 6,942,627 B2 | 9/2005 | Huitema |
| 6,099,570 A | 8/2000 | Livet | | 6,942,694 B2 | 9/2005 | Liddicoat |
| 6,110,182 A | 8/2000 | Mowlai-Ashtiani | | 7,018,418 B2 | 3/2006 | Amrich |
| 6,120,543 A | 9/2000 | Meesenburg | | 7,029,477 B2 | 4/2006 | Grimm |
| 6,132,468 A | 10/2000 | Mansmann | | 7,048,741 B2 | 5/2006 | Swanson |
| 6,139,581 A | 10/2000 | Engh | | 7,060,074 B2 | 6/2006 | Rosa |
| 6,165,223 A | 12/2000 | Metzger | | 7,077,867 B1 | 7/2006 | Pope |
| 6,171,340 B1 | 1/2001 | McDowell | | 7,104,966 B2 | 9/2006 | Shilber |

| Patent No. | Date | Name |
|---|---|---|
| 7,104,996 B2 | 9/2006 | Bonutti |
| 7,141,053 B2 | 11/2006 | Rosa |
| 7,172,596 B2 | 2/2007 | Coon |
| 7,175,630 B2 | 2/2007 | Farling |
| 7,241,298 B2 | 7/2007 | Nemec |
| 7,247,157 B2 * | 7/2007 | Prager et al. .............. 606/64 |
| 7,326,252 B2 | 2/2008 | Otto |
| 7,344,541 B2 | 3/2008 | Haines |
| 7,371,240 B2 | 5/2008 | Pinczewski |
| 7,422,605 B2 | 9/2008 | Burstein |
| 7,491,235 B2 | 2/2009 | Fell |
| 7,922,771 B2 | 4/2011 | Otto |
| 2001/0018615 A1 | 8/2001 | Biegun |
| 2001/0044627 A1 | 11/2001 | Justin |
| 2001/0049558 A1 | 12/2001 | Liddicoat |
| 2002/0055784 A1 | 5/2002 | Burstein |
| 2002/0103541 A1 | 8/2002 | Meyers |
| 2002/0107576 A1 | 8/2002 | Meyers |
| 2002/0120340 A1 | 8/2002 | Metzger |
| 2002/0161447 A1 | 10/2002 | Salehi |
| 2002/0183760 A1 | 12/2002 | McGovern |
| 2003/0028196 A1 | 2/2003 | Bonutti |
| 2003/0055501 A1 | 3/2003 | Fell |
| 2003/0055509 A1 | 3/2003 | McCue |
| 2003/0060882 A1 | 3/2003 | Fell |
| 2003/0060883 A1 | 3/2003 | Fell |
| 2003/0060884 A1 | 3/2003 | Fell |
| 2003/0060885 A1 | 3/2003 | Fell |
| 2003/0069585 A1 | 4/2003 | Axelson |
| 2003/0069591 A1 | 4/2003 | Carson |
| 2003/0093156 A1 | 5/2003 | Metzger |
| 2003/0130665 A1 | 7/2003 | Pinczewski |
| 2003/0158606 A1 * | 8/2003 | Coon et al. .............. 623/20.15 |
| 2003/0181986 A1 | 9/2003 | Buchholz |
| 2003/0208122 A1 | 11/2003 | Melkent |
| 2003/0212413 A1 | 11/2003 | Wilk |
| 2004/0039396 A1 | 2/2004 | Couture |
| 2004/0044414 A1 | 3/2004 | Nowakowski |
| 2004/0122305 A1 | 6/2004 | Grimm |
| 2004/0152970 A1 | 8/2004 | Hunter |
| 2004/0153066 A1 | 8/2004 | Coon |
| 2004/0199249 A1 | 10/2004 | Fell |
| 2004/0199250 A1 | 10/2004 | Fell |
| 2004/0249467 A1 | 12/2004 | Meyers |
| 2004/0249471 A1 | 12/2004 | Bindseil |
| 2004/0267363 A1 | 12/2004 | Fell |
| 2005/0033424 A1 | 2/2005 | Fell |
| 2005/0149038 A1 | 7/2005 | Haines |
| 2005/0149039 A1 | 7/2005 | Haines |
| 2005/0149040 A1 | 7/2005 | Haines |
| 2005/0171604 A1 | 8/2005 | Michalow |
| 2005/0283251 A1 * | 12/2005 | Coon et al. .............. 623/20.34 |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0052875 A1 | 3/2006 | Bernero |
| 2006/0058882 A1 | 3/2006 | Haines |
| 2007/0078517 A1 | 4/2007 | Engh |
| 2007/0179607 A1 | 8/2007 | Hodorek |
| 2008/0154270 A1 | 6/2008 | Haines |
| 2009/0076514 A1 | 3/2009 | Haines |
| 2009/0082773 A1 | 3/2009 | Haines |
| 2009/0138018 A1 | 5/2009 | Haines |
| 2010/0100192 A1 | 4/2010 | Haines |

FOREIGN PATENT DOCUMENTS

| | | |
|---|---|---|
| EP | 0121142 | 10/1984 |
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| GB | 1409150 | 10/1975 |
| GB | 2007980 | 7/1982 |
| GB | 2296443 | 7/1996 |
| GB | 2324249 | 10/1998 |
| GB | 2335145 | 9/1999 |
| JP | 02-501806 | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-243143 | 9/1990 |
| JP | 239861 | 9/1990 |
| JP | 02-246971 | 10/1990 |
| JP | 2002-274214 | 11/1990 |
| JP | 03-032663 | 2/1991 |
| JP | 04-297254 | 10/1992 |
| JP | 04-361746 | 12/1992 |
| JP | 05-003880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-237941 | 8/1994 |
| JP | 7-501966 | 3/1995 |
| JP | 7-116185 | 5/1995 |
| JP | 7-136200 | 5/1995 |
| RU | 2121319 | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO 97/05827 | 2/1997 |
| WO | WO97/29703 A1 | 8/1997 |
| WO | WO97/29704 A1 | 8/1997 |
| WO | WO 9820817 | 5/1998 |
| WO | WO 99/27872 | 6/1999 |
| WO | WO 99/30649 | 6/1999 |
| WO | WO 01/13825 | 3/2001 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

File History for U.S. Appl. No. 11/075,840, filed Mar. 8, 2005.
U.S. Appl. No. 11/075,552, Inventor: Haines, filed Mar. 8, 2005.
U.S. Appl. No. 11/825,857, Inventor: Haines, filed Jul. 9, 2007.
File History for U.S. Appl. No. 11/049,634, filed Feb. 5, 2005.
File History for U.S. Appl. No. 11/074,599, filed Mar. 8, 2005.
File History for U.S. Appl. No. 11/075,553, filed Mar. 8, 2005.
Whiteside Ortholoc Total Knee System, Dow Corning Wright, pp. ZH000109679-ZH000109690.
Zimmer, Insall/Burnstein II, *Modular Knee System*, Surgical Technique, pp. ZH000109691-ZH000109710.
Zimmer, The Miller/Galante Advantage: Total Knee System, pp. ZH000156953-ZH000156968.
U.S. Appl. No. 12/638,692, filed Jan. 4, 1977, Klawitter.
Freeman Samuelson, *Total Knee System*, published by Biomet, Inc., 1994 ("Biomet Brochure") (Attached as Exhibit F).
Freeman, Mark II *Total Knee Replacement System*, published 1985 (Attached as Exhibit G).
Protek F/S Modular Total Knee Replacement System, pp. 1-57, published by Protek in Jan. 1991 (Attached as Exhibit H).
*Low Contact Stress Meniscal Bearing Unicompartmental Knee Replacement: Long-Term Evaluation of Cemented and Cementless Results*, Journal of Orthopaedic Rheumatology (presented at the 57$^{th}$ Annual American Academy of Orthopaedic Surgeons Meetings, New Orleans, LA, Feb. 11, 1990), Bates No. DEP00004096-DEP00004107.
N.J. Unicompartmental Knee, Dated Sep. 15, 1989, Bates No. DEP00004108-DEP00004116.
Buechel, Frederick F., *NJ LCS Unicompartmental Knee System with Porocoat*, dated Oct. 24, 1994, Bates No. DEP000004117-DEP00004130.
Buechel, Frederick F. *NJ LCS Unicompartmental Knee System with Porocoat*, 1994, Bates No. DEP00004131-DEP00004141.
Buechel, Frederick F. *NJ LCS Unicompartmental Knee System with Porocoat*, 1994, Bates No. DEP00004142-DEP00004152.
Engh, et al., *The AMK Total Knee System, Design Rationale and Surgical Procedure*, dated 1989, Bates No. DEP00004153-DEP00004201.
*Advertising Proteck Mark II PCR Total Knee Replacement System*, Journal of Bone and Joint Surgery, 1987, Bates No. DEP00004202-DEP00004230.
Protek, *Parts Brochure for Mark II Protek*,1987, Bates No. DEP00004231-DEP00004235.
Chapman, Michael W., *Operative Orthopaedics*, vol. 1, Published by J.B. Lipponcott Co., Philadelphia, dated 1988, Bates No. DEP00004236-DEP00004247.
American Academy of Orthopaedic Surgeons, *Flyer from 57$^{th}$ Annual American Academy of Orthopaedic Surgeons Meeting*, Februay 13, 1990, Bates No. DEP00004248-DEP00004251.
Crossett et al., *AMK Congruency Instrument System, Surgical Technique*, dated 1997, Bates No. DEP00004252-DEP00004267.
Engh et al., *AMK Surgical Technique*, Bates No. DEP00004268-DEP00004298, dated 1989.
Engh et al., *AMK Surgical Technique*, Bates No. DEP00004299-DEP00004329, dated 1989.
Crenshaw, A.H., *Campbell's Operative Orthopaedics*, 4$^{th}$ Edition, vol. 1, Bates No. DEP00004330-DEP00004333, dated 1963.
Howmedica, *Duraconcept, Design Concepts of the Duracon Total Knee System*, Bates No. DEP00004337-DEP00004337, dated 1993.
Freeman et al., *Total Knee System*, Bates No. DEP00004350-DEP00004361, Published prior to Jun. 7, 1994.
Freeman et al., *F/S Modular Total Knee Replacement System-SICOT*, 90 Edition, Bates No. DEP00004362-DEP00004373, dated 1990.
Buechel, Frederick F., *Howmedica Product Catalog*, Bates No. DEP00004374-DEP00004375, dated 1994.
Massarella, Antony, *Interax Bulletin, No. 6, Tibial Intramedullary Alignment Surgical Technique*, Bates No. DEP00004387-DEP0000-4390, dated Feb. 23, 1994.
Desjardins et al., *Interax Operative Technique*, Bates No. DEP00004391-DEP00004411, dated 1994.
Desjardins et al., *Interax Total Knee Operative Technique: Monogram Total Knee Instruments*, Bates No. DEP00004412-DEP00004432, dated 1993.
Howmedica, *Interax Tibial IM*, Bates No. DEP00004433-DEP00004433, dated 1994.
Depuy, *LCS Uni PMA Data from FDA Website*, Bates No. DEP00004434-DEP00004434, dated 1991.
Briard et al., *LCS Uni Unicompartmental Knee System with Porocoat*, Bates No. DEP00004452-DEP00004462, dated 1991.
Freeman et al., *Mark II Total Knee Replacement System*, Bates No. DEP00004463-DEP00004492, dated 1985.
Buechel, Frederick F., *NJ LCS Unicompartmental Knee System with Porocoat*, Bates No. DEP00004493-DEP00004503, dated 1994.
Chapman, Michael W. *Operative Orthopaedics*, vol. 3, 2$^{nd}$ Edition, Published by J.B. Lipponcott Co., Bates No. DEP00004504-DEP00004508, dated 1993.
Biomet, *Oxford Meniscal Knee Phase II Unicompartmental Replacement*, Bates No. DEP00004509-DEP00004515, Published prior to Jun. 7, 1994.
Scott et al., *P.F.C. Sigma Unicompartmental Knee System*, Bates No. DEP00004531-DEP00004539, dated 1998.
Freeman et al., *F/S Modular Total Knee Replacement System*, Bates No. DEP00004540-DEP00004596, dated 1990.
Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates No. DEP00004752-DEP00004763.
Scott et al., *Unicompartmental and High Tibial Osteotomy for Osteoarthritis of the Knee*, Journal of Bone and Joint Surgery, vol. 63-A, No. 4, Apr. 1, 1981, Bates No. DEP00004764-DEP00004775.
Thornhill, Thomas S., *Unicompartmental Knee Arthroplasty Clinical Orthopaedics and Related Research*, No. 205, Apr. 1, 1986, pp. 121-131, Bates No. DEP00004776-DEP00004791.
Forst et al., *A Special jg for Tibial Resection for the Implantation of GSB-Knee-Prostheses in Problematic cases*, pp. 162-166, dated Jun. 1, 1984, Bates No. DEP00004838-DEP00004842.
Ingillis et al., *Revision Total Knee Replacement Techniques in Orthopedics*, dated Apr. 1, 1990, Bates No. DEP00005583-DEP00005592.
Uvehammer et al., "In Vivo Kinematics of Total Knee Arthroplasty: Concave Versus Posterior-Stabilised Tibial Joint Surface", vol. 82-B, No. 4, May 2000, pp. 499-505.
T.D.V. Cooke et al., *Universal Bone Cutting Device for Precision Knee Replacement Arthroplasty and Osteotomy*, 7 J. Biomed. Eng'g 45, 47, col. 2,11. 52-57 (1985).
E. Marlowe Goble and Daniel F. Justin, *Minimally invasive total knee replacement: principles and technique*, Orthop. Clin. N. Am. 35 (2004) 235-245.
Whiteside Ortholoc Total Knee System: Surgical Procedure, Dow Corning Wright, pp. WMT000001-WMT000040, Jun. 1985.
Zimmer, Insall/Burstein II, *Constrained Condylar: Modular Knee System*, 35 pages, copyright 1989.
File History for U.S. Appl. No. 12/187, 210, filed Aug. 6, 2008.
File History for U.S. Appl. No. 11/075,842, filed Mar. 8, 2005.
File History for U.S. Appl. No. 11/075,828, filed Mar. 8, 2005.
U.S. Appl. No. 12/171,843, Inventor: Haines, filed Jul. 11, 2008.

* cited by examiner

PRIOR ART FEMORAL REFERENCE POINTS

*Fig.* 22

ND APPARATUS FOR
ENHANCED RETENTION OF PROSTHETIC
IMPLANTS

CLAIM TO PRIORITY

The present invention claims priority to U.S. Provisional Application No. 60/551,096, filed Mar. 8, 2004, entitled, "METHODS AND APPARATUS FOR ENHANCED RETENTION OF PROSTHETIC IMPLANTS," and claims priority to U.S. Provisional Application No. 60/551,080, filed Mar. 8, 2004, entitled, "METHODS AND APPARATUS FOR PIVOTABLE GUIDE SURFACES FOR ARTHROPLASTY," and claims priority to U.S. Provisional Application No. 60/551,078, filed Mar. 8, 2004, entitled, "METHODS AND APPARATUS FOR MINIMALLY INVASIVE RESECTION," and claims priority to U.S. Provisional Application No. 60/551,631, filed Mar. 8, 2004, entitled, "METHODS AND APPARATUS FOR CONFORMABLE PROSTHETIC IMPLANTS," and claims priority to U.S. Provisional Application No. 60/551,307, filed Mar. 8, 2004, entitled, "METHODS AND APPARATUS FOR IMPROVED CUTTING TOOLS FOR RESECTION," and claims priority to U.S. Provisional Application No. 60/551,262, filed Mar. 8, 2004, entitled, "METHODS AND APPARATUS FOR IMPROVED DRILLING AND MILLING TOOLS FOR RESECTION," and claims priority to U.S. Provisional Application No. 60/551,160, filed Mar. 8, 2004, entitled, "METHODS AND APPARATUS FOR IMPROVED PROFILE BASED RESECTION," and is a continuation-in-part of U.S. patent application Ser. No. 11/036,584, filed Jan. 14, 2005, entitled, "METHODS AND APPARATUS FOR PINPLASTY BONE RESECTION," which claims priority to U.S. Provisional Application No. 60/536,320, filed Jan. 14, 2004, and is a continuation-in-part of U.S. patent application Ser. No. 11/049,634, filed Feb. 2, 2005 now abandoned, entitled, "METHODS AND APPARATUS FOR WIREPLASTY BONE RESECTION," which claims priority to U.S. Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for prosthetic implant devices. More particularly, the present invention relates to prosthetic implants for joints that include structure permitting the enhanced retention of the prosthetic implants.

2. Background Art

The replacement or augmentation of joints with artificial or prosthetic implants is well known in the field of orthopedics. Total knee arthroplasty (TKA) procedures involving the replacement of the knee joint are a good example. U.S. Publ. Appl. 2003/0028196A1 and the PFC RP Knee Replacement manual provide a good background for the techniques and devices used as part of these TKA procedures.

Most typically, a prosthetic implant is provided either with a long post or peg that is seated in a hole drilled into the longitudinal axis of the bone, such as for a tibial implant. In some cases, the peg is provided with a longitudinal fin running anterior-to-posterior that mates with a corresponding channel cut into the bone, such as for a femoral implant. U.S. Publ. Appl. 2003/0100953A1 describes a knee implant that has a pair of shaped pegs for the tibial implant and a longitudinal fin for the femoral implant that includes a peg with external recess features to assist in the fixation of the femoral implant. In one embodiment of the knee implant procedures described in U.S. Publ. Appl. 2003/0028916A1, a TKA femoral implant is described which utilizes a medio-laterally oriented protruding slot on the upper surface of the implant to interface with the femoral surface instead of a peg. The purpose and arrangement of this sideways oriented feature of this femoral implant is to permit the implant to be slid into place from a minimally invasive incision in either the lateral or medial side, as compared to the conventional approach where the major incisions for the TKA procedure are made primarily on the anterior (front) side of the knee.

It would be desirable to provide for an orthopedic prosthetic implant that could be implanted more consistently and effectively, yet be adaptable for implantation by minimally invasive procedures.

SUMMARY OF THE INVENTION

The present invention is a prosthetic implant that utilizes lateral retaining structures as part of the interior surface of the implant, instead of pegs and longitudinal fins. The lateral retaining structures serve to more effectively secure and retain the implant while reducing the overall size and mass of the implant, decreasing bone volume lost during the procedure and facilitating minimally invasive surgical techniques. In one embodiment, the prosthetic implant is provided with one or more T-shaped members extending from the inner surface of the implant, with the cross-member of the T-shaped member forming the laterally retaining structure. In this embodiment, the T-shaped members preferably mate with a correspondingly shaped channel formed in the bone and are inserted into that channel at one or more oversize locations along the channel. In another embodiment, the prosthetic implant is provided with one or more grommet features on the inner surface of the implant that are laterally secured with a force fitted cross pin inserted through an aperture formed by the grommet feature. In this embodiment, the apertures of the grommet features are preferably commonly aligned with the holes used to secure the cutting guides. Alternatively, the injection of flowable materials such as bone cement or polymethymethacrylate could be injected or placed so as to 'form' a cross pin type retention feature.

The present invention provides for embodiments of prosthetic implant designs facilitating intraoperative and postoperative efficacy and ease of use. The present invention utilizes a number of embodiments of prosthetic implants, or prosthetic implant features to facilitate clinical efficacy of arthroplasty procedures. The overriding objects of the embodiments are to facilitate short and long terms fixation of the implant with respect to the bone, enable bone preservation to facilitate ease and efficacy of revision, and/or to take advantage of the natural physiological phenomenon determining bone growth response to load stimuli.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which.

DETAILED DESCRIPTION OF THE PREFERRED EMBODIMENTS

It should be noted that, in many of the figures, the cut surface created by the cutting tool are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity.

FIGS. 4 through 7 generally represent prosthesis and prosthesis fixation feature embodiments of the present invention.

Figure 4:
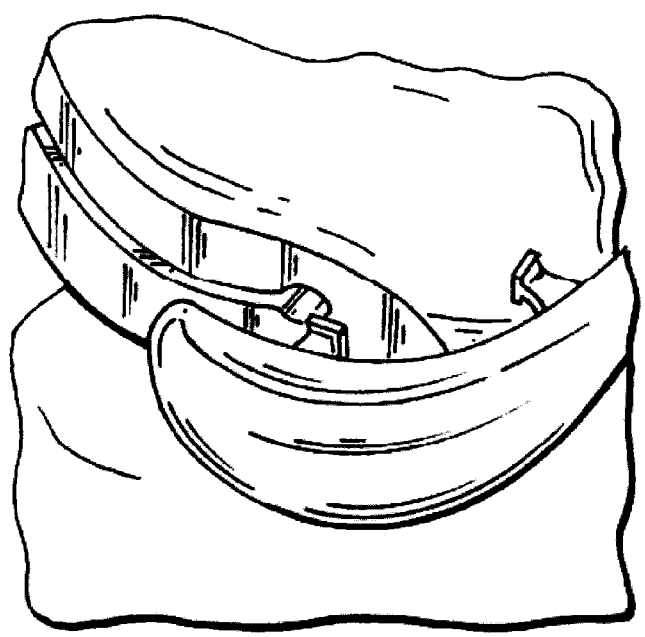
Figure 5:
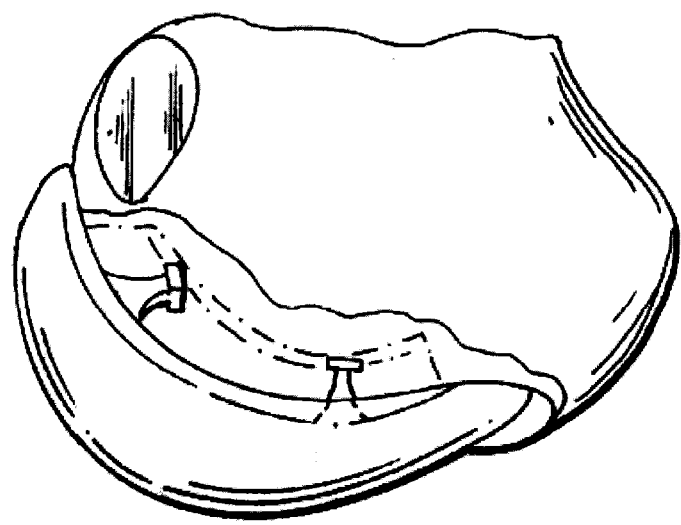
Figure 6:
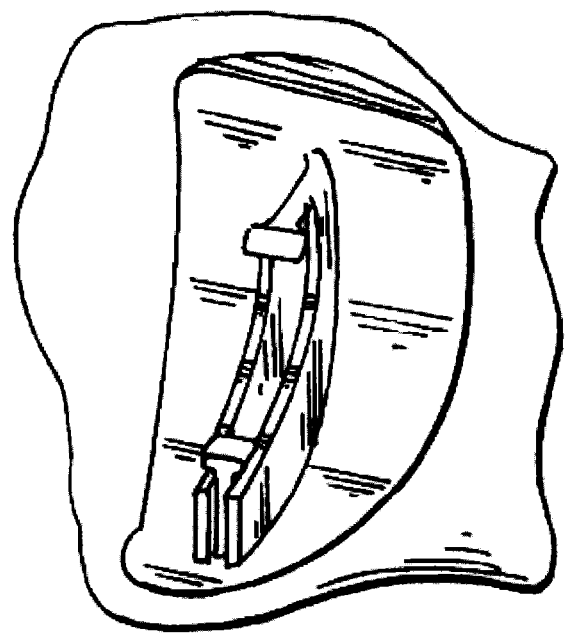
Figure 7:
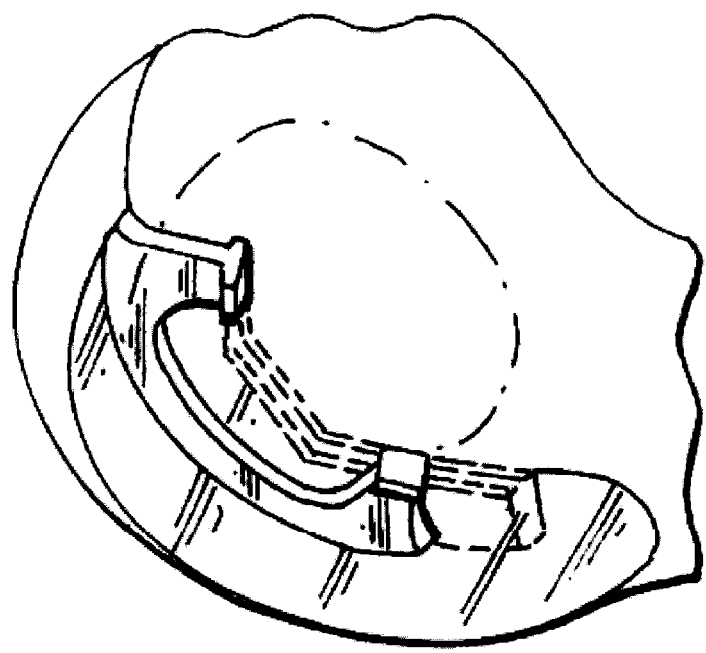
Figure 8:
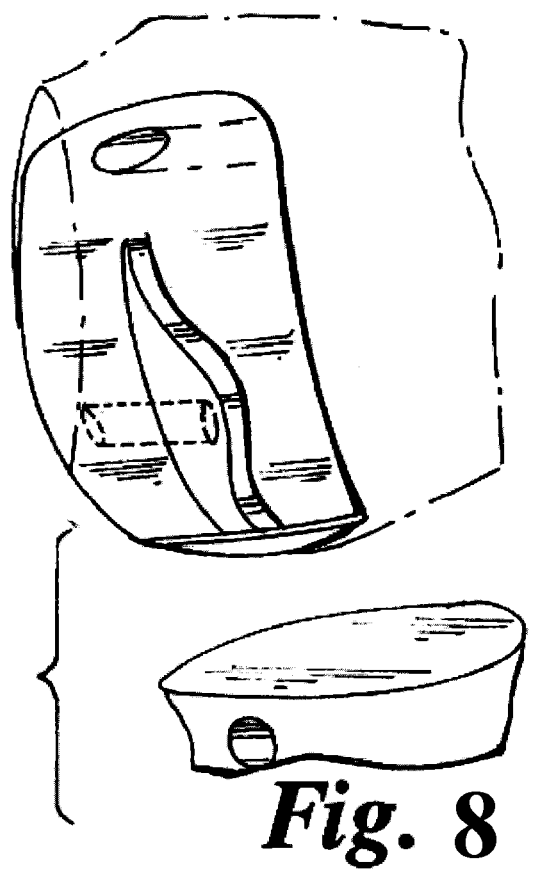

FIGS. 4 through 7 show representations of a tongue in groove fixation feature applied to a Unicondylar femoral component enabling anterior insertion of one tongue element into a 't-slot' style groove formed in bone and a progressively increasing press fit obtained by forcing the implant posteriorly, as is represented in comparing FIGS. 4 and 5. The t-slot feature, or groove, formed in the femur is easily formed by, in one embodiment, providing a trial component possessing a contoured groove and slot for guiding a t-slot cutter along its length. Such a contour groove would be responsible for controlling the depth of the t-slot in the bone with respect to the cut surface to which the implant fixation surface is attached, while the slot in the trial would dictate the mediolateral location of the t-slot style groove. It is preferable to include an aperture in the slot and/or contour groove in the trial component to allow for insertion and plunging of the wider T cutting surfaces prior to sweeping.

Figure 11:
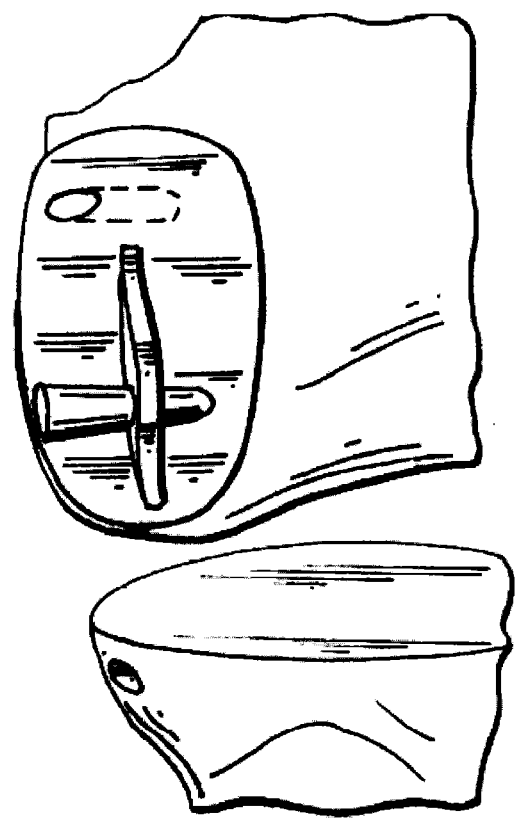

Alternatively, FIGS. 8 through 17 represent combinations of finned and/or crosspinned implants. It should be noted that the AP Fin Profile of the fin may be linear as shown in FIG. 11 (in other words, the fin may be may be planar), or it could be slightly tapered to achieve an interference fit with the walls of the groove as the implant fixation surfaces are forced into contact with the cut surfaces to which they are mated (see FIGS. 12 through 14), or it could be curved as looked at from the viewpoint of FIG. 11 to further provide stability of fixation (this curve could be a single curve or spline or sinusoidal curve, in one embodiment of the present invention allowing for a multiaxial interference fit between the fin and bone to facilitate fixation and avoid deleterious levels of postoperative micromotion). Interestingly, the fixation aperture created to fix a cutting guide to the bone could be utilized to cross pin a flange or fin of a femoral prosthesis. It should be noted that although the embodiment shown is a Unicondylar femoral prosthesis, this concept could be applied to tibial, femoral, or patellofemoral prostheses in any application, or in other joint, trauma, spine, or oncology procedures, as is generally represented in FIGS. 21 through 28.

Figure 9:
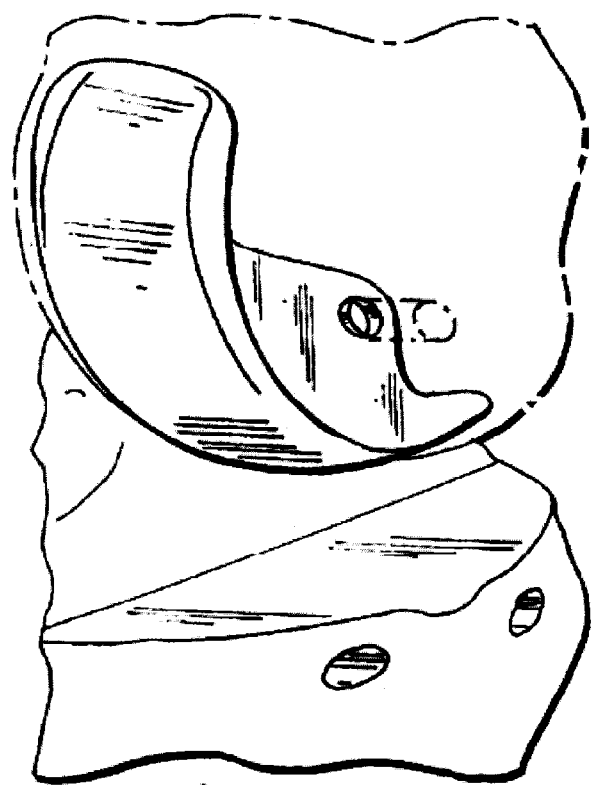
Figure 10:
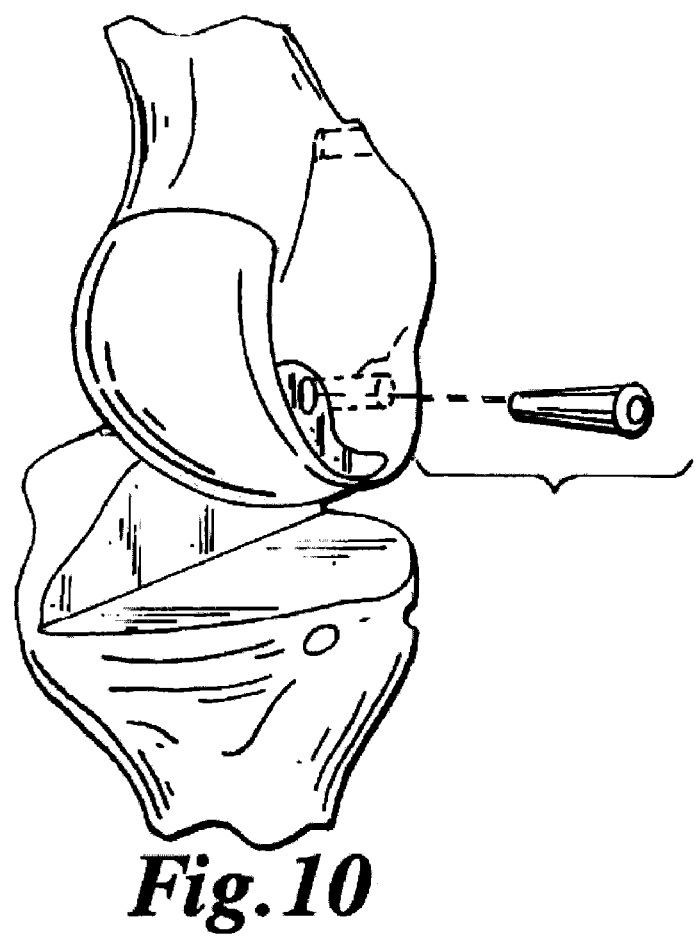
Figure 16:
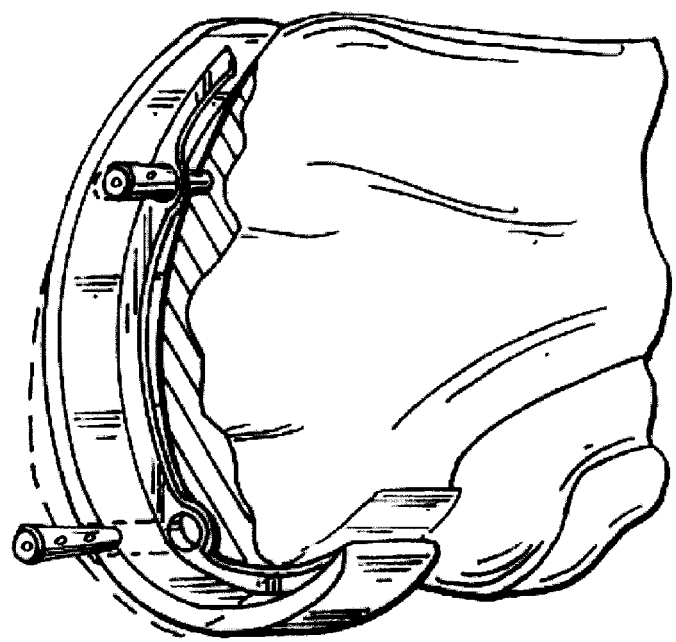
Figure 17:
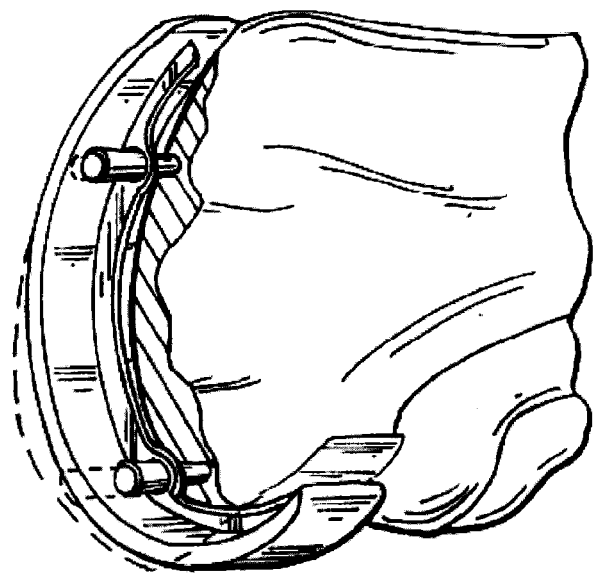

In FIGS. 10 through 17, a tapered pin is used to engage the cross pin hole in the fin of the prosthesis. The tapered pin may be utilized to facilitate a resulting press fit between the pin and the fixation surfaces of the implant and/or ease of introducing the pin into the hole in the fin. The pin could be of any known material, but resorbable materials are especially interesting as they are 'consumed' by the body leaving minimal hardware within the body after a fairly predictable amount of time has passed. PLA/PGA compositions, Tricalcium Phosphate, allograft and autograft bone, bone substitutes, and the aforementioned slurry type compositions may serve well. Alternatively, bone cement or other liquid or semi-liquid material may be injected into the portals/apertures to achieve intimate interdigitation, and the crosspins optionally inserted thereafter, but prior to complete hardening or curing. Alternatively, the crosspin(s) could be hollow with radially extending holes as shown in FIG. 16 allowing the pins to be inserted and then have bone cement injected into them and up under the implant. Alternatively, the cross pin could be threaded to engage threads in the fin, or to engage the bone (both for short term stability and to facilitate removal) or both. In some embodiments, the cross pin hole can be tapered as shown in FIG. 9. These embodiments hold significant promise in both providing for intraoperatively stable for cemented or cementless fixation as well as facilitating long-term biological ingrowth. It should be noted that the use of multiple holes, pins, and apertures in the prosthesis could be used and that the holes in the bone need not be fixation holes to which guides are attached. Also it should be noted the condylar sections, and patellofemoral sections of the implant could be wholly separate, modularly joined, be composed of a dual condylar prosthesis and separate patellofemoral prosthesis, or any combination of the above. Although the bone/implant interface shown is curved in two planes, these concepts apply to implants with 3 planar curved geometry (where the cutting path and cutting profiles of the resected surface geometry and therefore the fixation surface geometry do not remain in two planes through the entirety of the cutting path, or where the cutting path is contained within multiple or single curved surfaces), entirely planar geometries, or anything in between.

Figure 12:
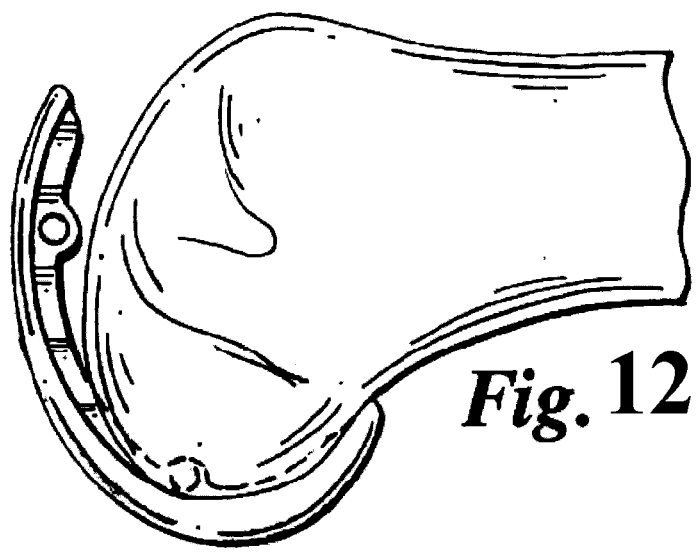
Figure 13:
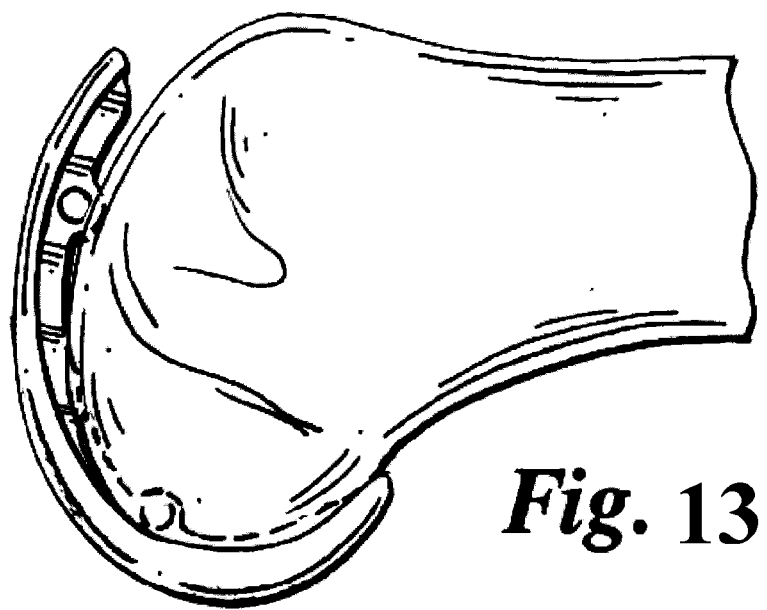
Figure 14:
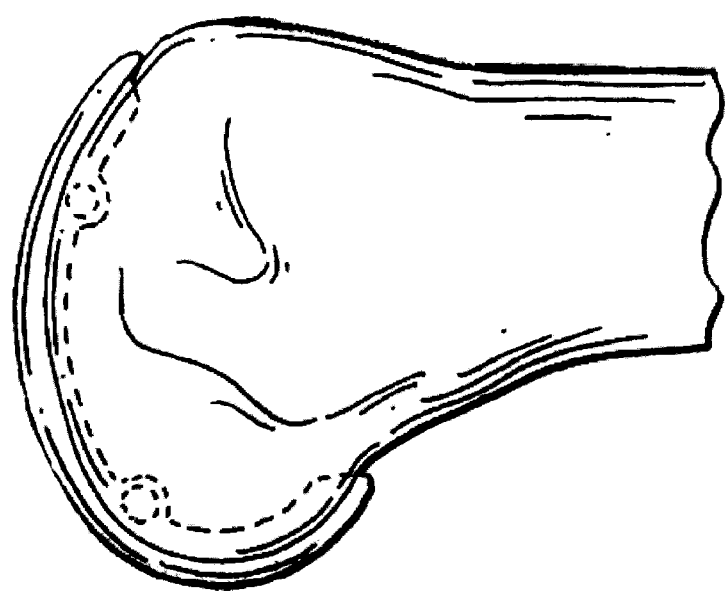
Figure 15:
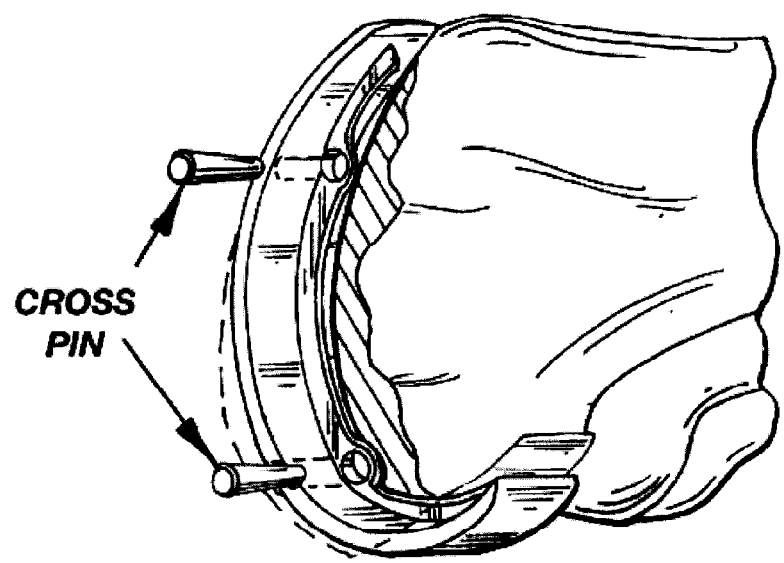

FIGS. 12 through 17 demonstrate another embodiment of the present invention allowing for benefits well above and beyond those of the prior art. This will be referred to herein as a BMO Prosthesis or BMO Cortical type implant (Biomechanical Optimization Prosthesis). This embodiment has several applications. For instance, if the resected surfaces will to vary significantly from the fixation surface geometries, as may be seen in unguided kinematic resection, it may be advantageous to implement fixation surface geometries that can conform to variation in resection geometry. Most implant materials in joint replacement are thought of as being rigid, and that their rigidity is a desirable characteristic for achieving stable fixation. In the case of surface replacement, that is not necessarily the case. Anecdotally, picture a bar of aluminum 2 inches square and 5 inches long—now picture trying to manually bend it. At these dimensions, aluminum is rigid; however, it is obvious that aluminum foil is not so rigid. The point to this is that very thin (less than 3 mm thick, probably closer to a range of 1.5 to 0.01 mm thick) sections of many metals, including implant grade metals and alloys including cobalt chrome, titanium, zirconium, and liquid metal™, can be processed into very thin forms capable of conforming to variations in the resected surface and yet still have bearing surfaces that are highly polished and provide significant contact area, where desirable, for bearing against the bearing or articular surfaces of the opposing implant. The construct or prosthesis resulting from applying the present invention to a femoral component in Unicondylar knee replacement, for example, may start out being a 1" wide be 3" long strip of 1.5 mm thick material curved in a manner to generally look like the curved cutting path and curved cutting profile of a natural, healthy femur. A process such as Tecotex from Viasys Healthcare of Wilmington, Mass. is used to remove material from the strip down to a nominal thickness of perhaps 0.1 mm thick while leaving multiple protruding 'hooks' (almost like the hook and eye concept of Velcro) emerging from the thin fixation surface to engage the bone. One or more fins can be attached or be made a continuous part of this construct as shown in FIG. 12. During insertion, the anterior most cross pin could lock that portion of the prosthesis in place, then the prosthesis could be wrapped around the remaining, more posteriorly resected surfaces and the posterior cross pin inserted (see FIG. 16). Alternatively, the fins can be located about the periphery of the articular surfaces of the condyle in the form of tabs and the cross pins or screws or tapered dowels, etc. known in the art inserted through holes in the tabs and into bone to fix the cortical implant. The combination of fins and tabs may also be useful. In using the tabs, it is critical to keep all features of the implanted device ultralow profile to avoid irritating the surrounding soft tissues (perhaps creating recesses in the bone underlying the tabs would be desirable to allow for a form of countersinking of the tabs and/or the pins or screws or other fixation devices).

Figure 1:
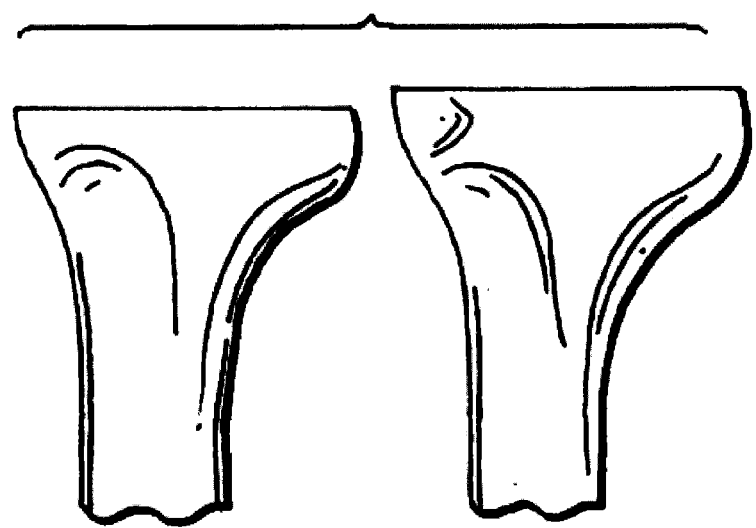
FIGS. 1-30 show various depictions of embodiments and methods in accordance with alternate embodiments of the present invention.
Figure 2:
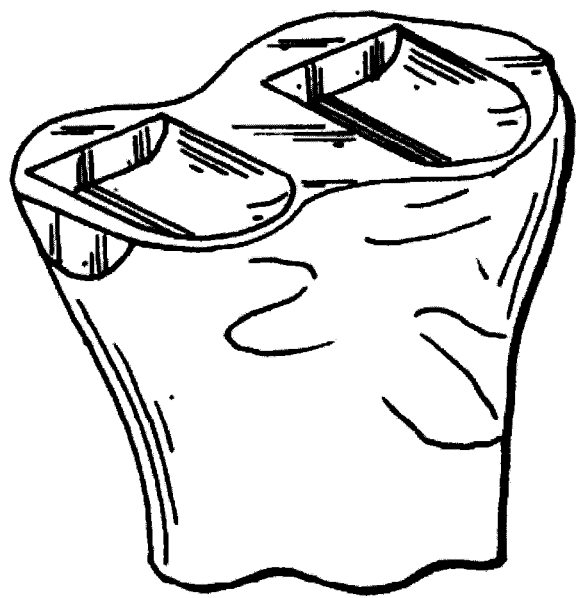
Figure 3:
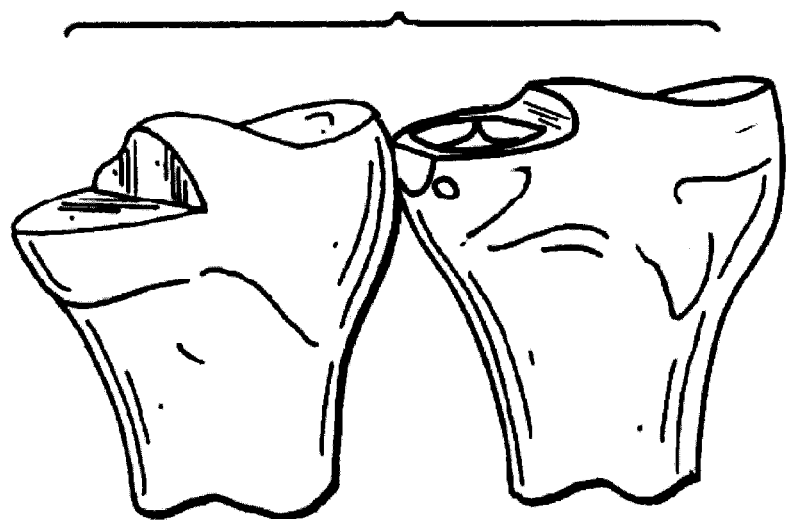

Another embodiment of the present invention would be to apply the aforementioned principals to tibial implant design and fixation methodologies. It should be obvious to one of ordinary skill in the art that the crosspin and/or tongue and groove configurations would provide for outstanding stability of tibial component fixation to living bone whether for conventional finned tibial components or the AP or ML fin embodiments of the present invention. FIGS. 1 through 3 represent, very generally, some of the basic primary cut surface geometries to which such implants may be attached (although the fin accommodating cuts are not shown). In regards to conventional state of the art tibial component designs, the implementation of the crosspin embodiments of the present invention will provide for attaining sufficiently robust cementless fixation of implant to bone that the currently substandard results of pressfit tibial components may be significantly improved upon.

The flexibility of the implant in accordance with the present invention allows the implant to conform to the resection surface and the stability of the crosspin fixation would assist in reducing interfacial micromotion known to inhibit bone ingrowth and fixation (this concept could be used with PMMA, but it is also desirable to avoid the tissue necrosis and bone preservation for revision issues associated with the use of bone cement if the patients health/comorbidities/indications allow). This kind of implant has some very interesting clinical benefits beyond simple bone preservation. Given how well this kind of conformable implant imparts load to underlying bone, thus avoiding stress shielding, it is possible not only to promote healthy bone ingrowth into and around the interfacial features, but the bearing contact and strains/stresses imparted to the bone could motivate the bone to change its shape (and therefore the shape of the conformable implant also changes over time because of the flexibility) to ideally conform to the tibial component bearing surface such that bearing stresses are carried through the broadest desirable contact area just like modeling/remodeling in a healthy unmodified joint).

Figure 18:
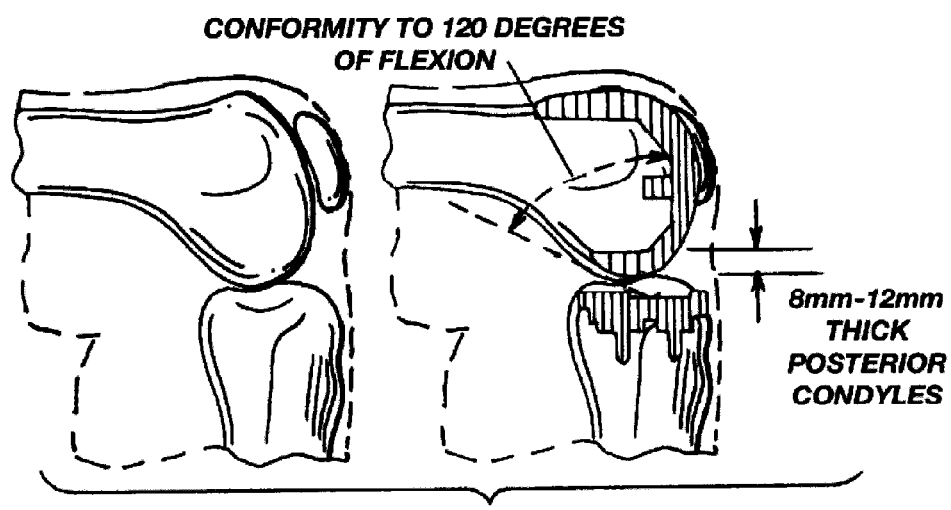
Figure 19:
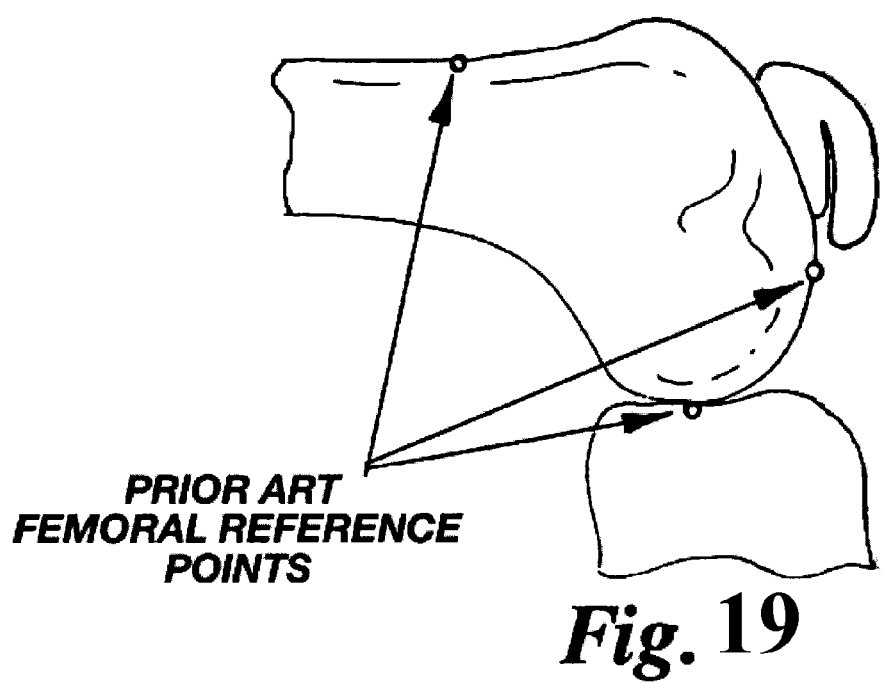
Figure 20:
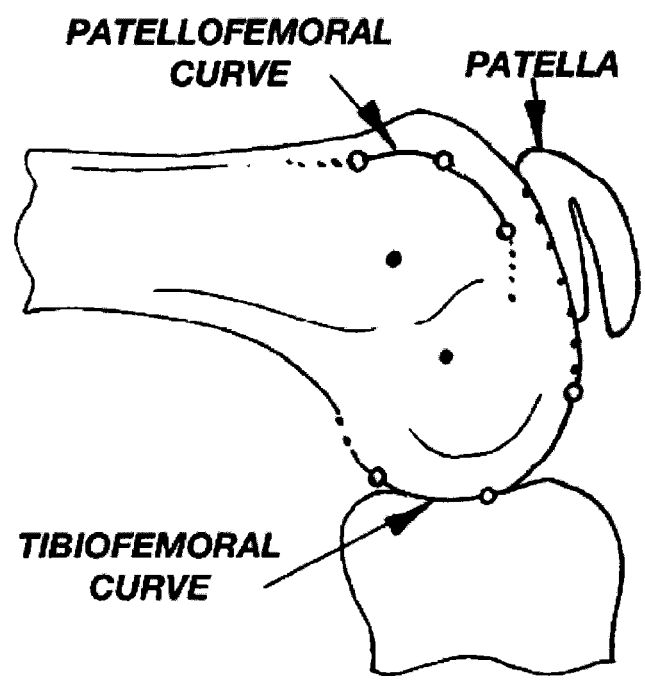
Figure 21:
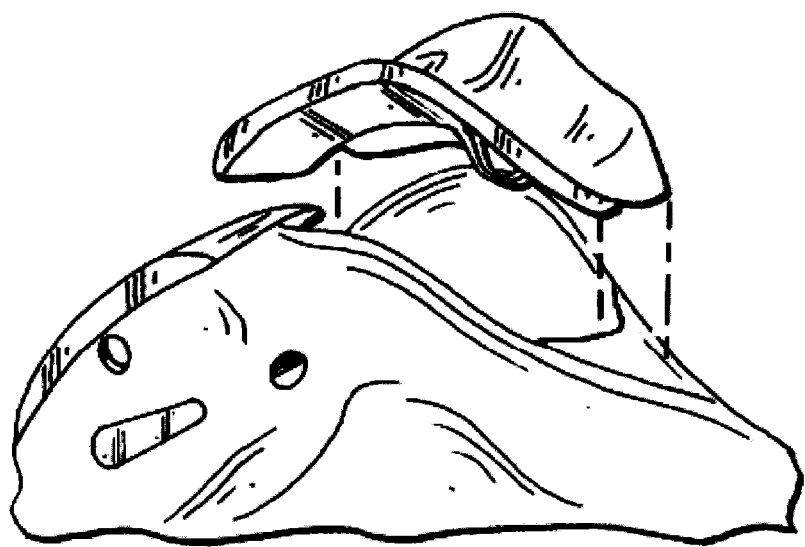
Figure 22:
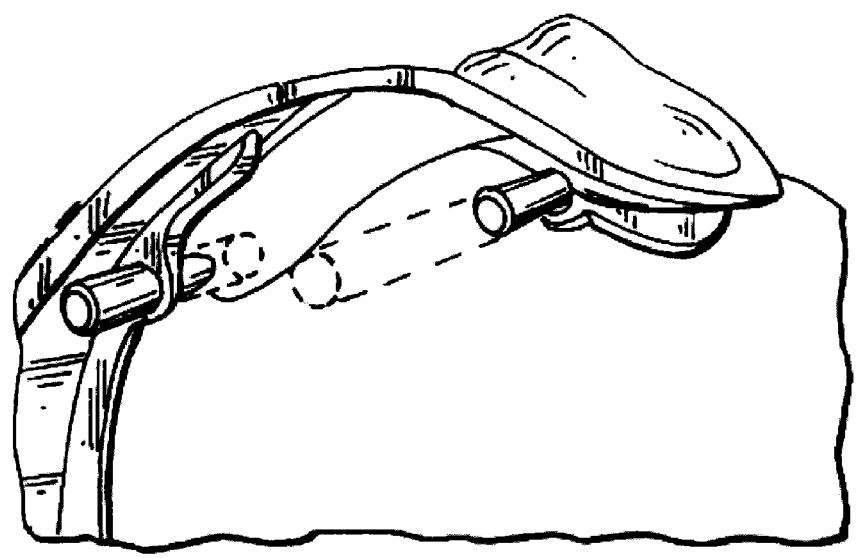
Figure 23:
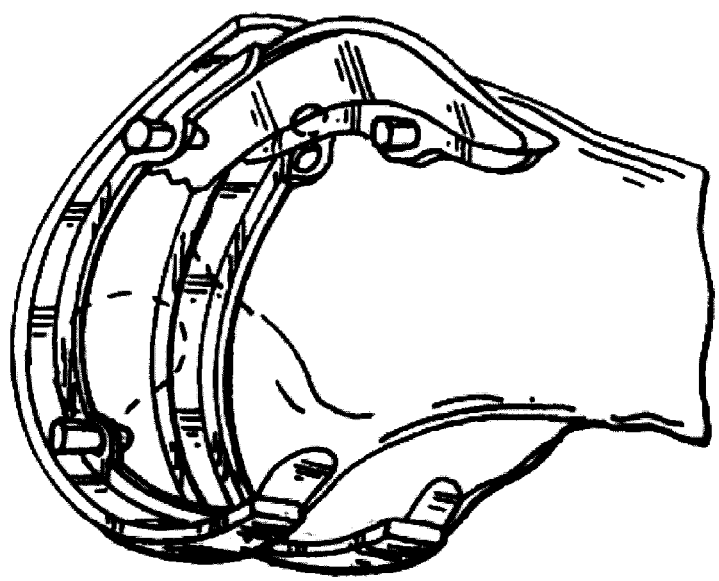

FIGS. 18 through 20 are an embodiment of the present invention that may prove to be a very usefully alternative to conventional rectilinear based referencing techniques. In essence, conventional alignment techniques, once having established appropriate flexion extension angulation and varus valgus angulation of desired implant location, reference the anterior cortex, distal most femoral condylar surface, and posterior most condylar surface (indicated in FIG. 19 by stars) to dictate the anterior posterior location, proximal distal location (otherwise known as distal resection depth), and appropriate implant size in determining the 'perfect' location and orientation for the appropriately sized implant (mediolateral location is normally 'eyeballed' by comparison of some visual reference of the mediolateral border surrounding the distal cut surface and some form of visual guide reference). These conventional techniques fail to directly reference the distinctly different anatomic bone features which dictate the performance of distinctly separate, but functionally interrelated, kinematic phenomena, and they also attempt to reference curvilinear articular surfaces by way of rectilinear approximations. The embodiment of the present invention is an alternative alignment technique with an object to overcome the errors inherent in prior art. As shown in FIG. 20, the femur possesses two distinct kinematic features and functions that lend themselves to physical referencing; the patellofemoral articular surface and the tibiofemoral articular surfaces, both of which are curved, more specifically these surfaces represent logarithmic curves that may be effectively approximated by arcs. The one codependency between the two articular functions, and therefore any geometric approximation made of them in referencing, is that they must allow for smooth kinematically appropriate articulation of the patella as it passes from its articulation with the trochlear groove (shown in blue in FIG. 20) to its articulation with intercondylar surfaces between the femoral condyles (shown in red in FIG. 20). Thus, knowing that three points define an arc and may be used to approximate a curve or sections of a curve, what is proposed is to use a referencing device which contacts at least one femoral condyle at three points to determine both an approximation of arc radius and centerpoint location, while independently or simultaneously referencing the trochlear groove at three points to determine both an approximation of arc radius and centerpoint location. The referencing system would further need to provide for the need of the articular surfaces of the trochlear articular surfaces to smoothly transition to those of the intercondylar surfaces. Armed with this information, a surgeon may most appropriately determine appropriate implant location and orientation.

Figure 24:
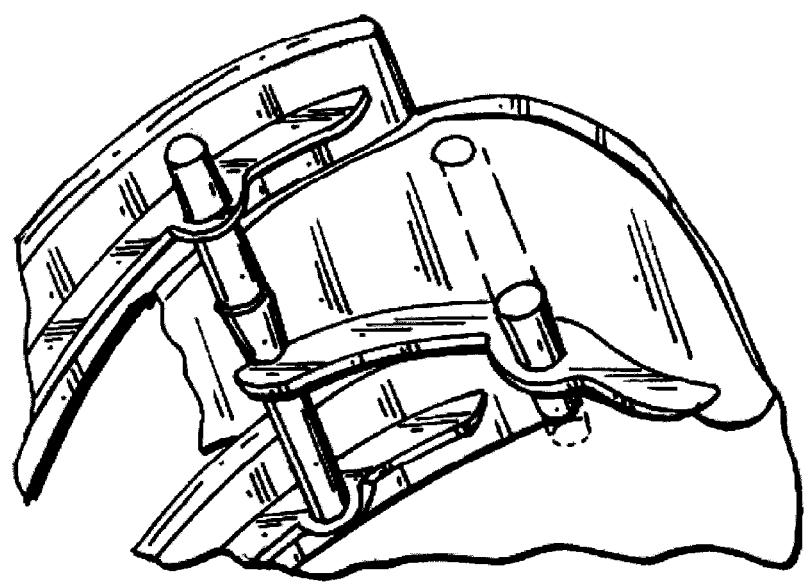
Figure 25:
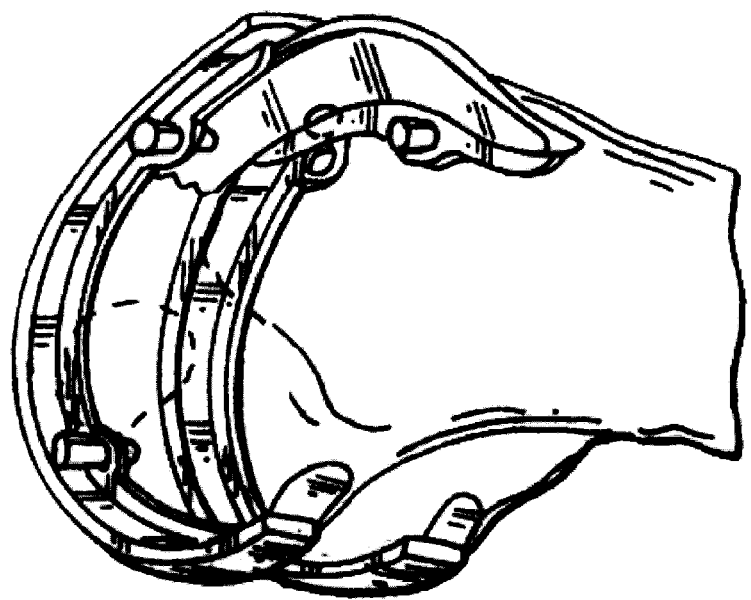
Figure 26:
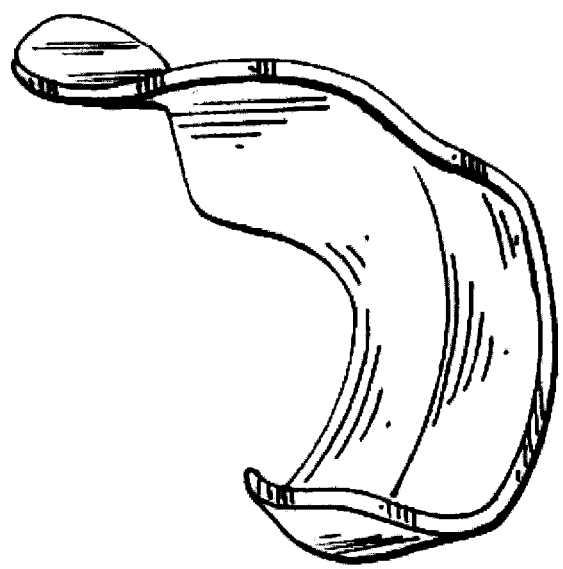
Figure 27:
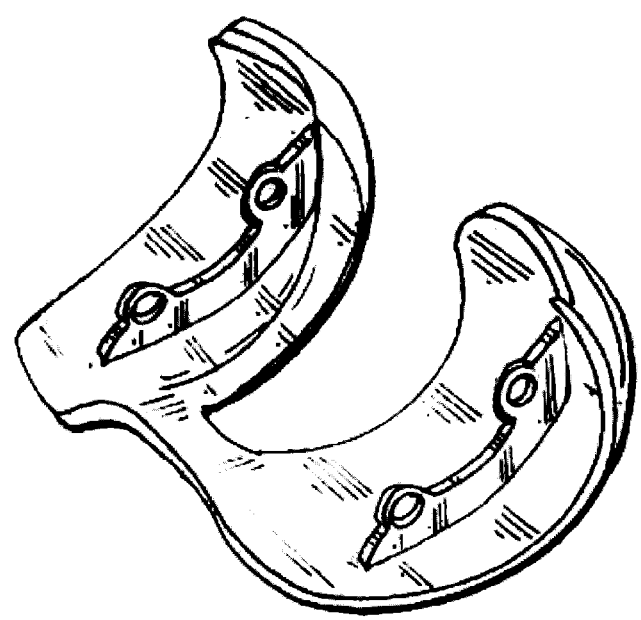
Figure 28:
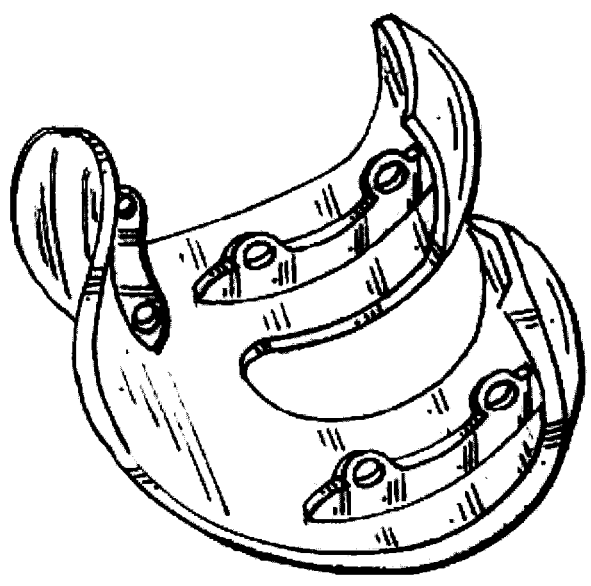
Figure 29:
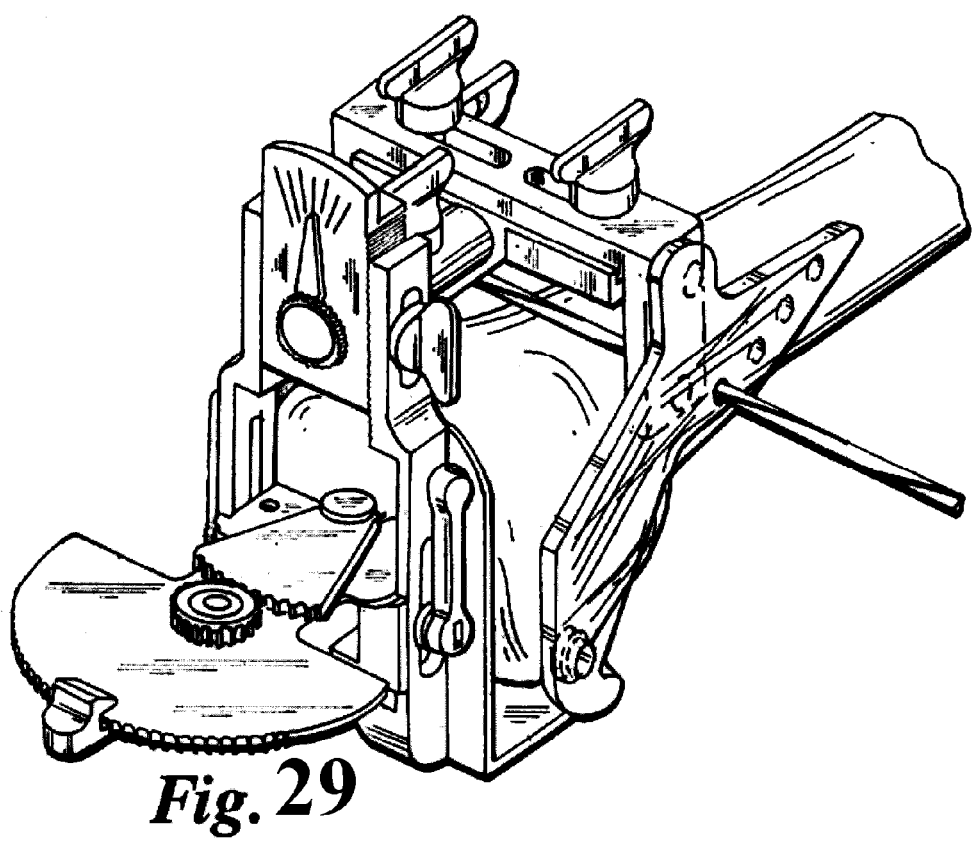
Figure 30:
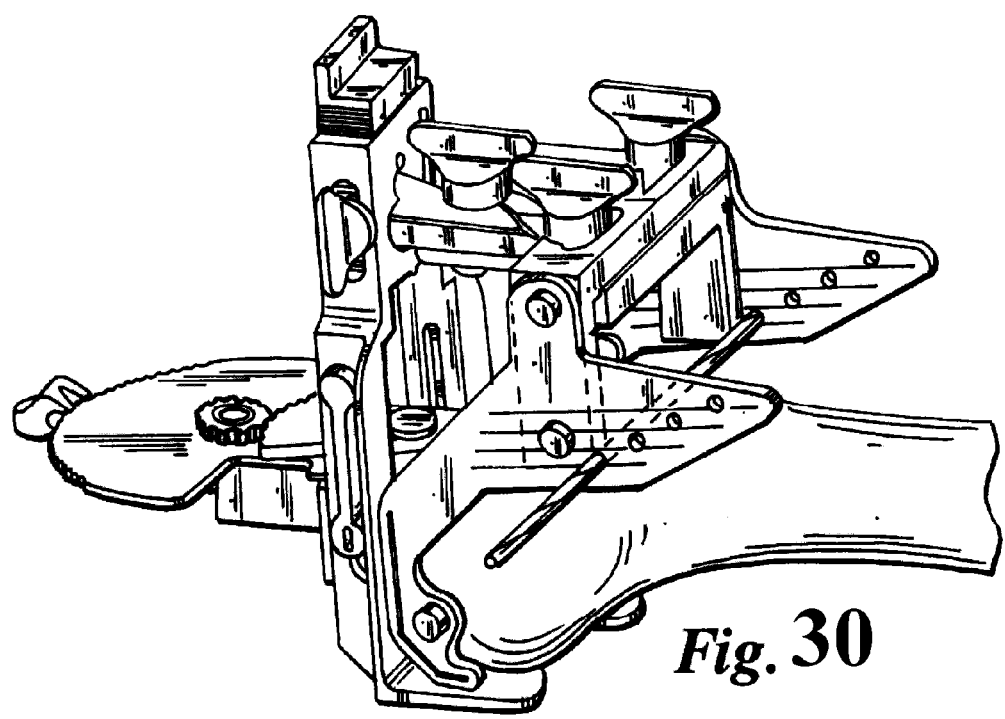

This embodiment of the present invention is especially useful in determining the proper location, orientation, and implant size for the modular tricompartment components shown in FIGS. 21 through 25, the non-modular implants shown in FIGS. 26 through 126, and standard implants where the appropriate size, location, and orientation would be determined by that which best mimics existing articular bone surfaces thus resulting in optimal postoperative kinematic function. FIG. 24 represents one method of fixing the patellofemoral implant with respect to the condylar implant(s) so as to maintain smooth transitional articulation. It should be noted that this crosspin method of interconnecting the separate components could be augmented by tongue and groove interlocking between the medial side of the condylar component shown and the lateral side of the patellofemoral component shown. What is critical is that the transition between the patellofemoral component and the condylar component surfaces responsible for patellofemoral articulation are and remain tangent at at least one point. FIGS. 29 and 30 represent an alignment guide that could be easily modified to accomplish the aforementioned 3 point referencing by addition or inclusion of dedicated or modular referencing means. Alternatively, surgical navigation methods could be implemented in registering these articular surfaces and determining the resulting idealized implant location(s) and orientation(s) as reflected by the geometry and/or kinematics of the joint.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed is:

1. An implantable orthopedic prosthesis for implantation on a bone during a knee arthroplasty procedure, the implantable prosthesis comprising:
    an implant body having a fixation surface adapted to mate and fixate to a resected articular surface of the bone and an articulation surface adapted to articulate with a second knee arthroplasty implant;
    at least one projection structure extending inwardly from the fixation surface of the implant body toward the bone; and
    means for laterally retaining the at least one projection structure such that, when the implant body fixation surface is in contact with the resected surface of the bone in an unloaded condition, as the means for laterally retaining is advanced in a first direction into a corresponding channel formed in the bone a preload force generated by the means for laterally retaining oriented in a second direction is exerted on the implant body biasing the fixation surface of the implant body against the resected surface of the bone and a compressive force is exerted between the corresponding channel and the means for laterally retaining, wherein the second direction is generally perpendicular to the first direction.

2. The implantable orthopedic prosthesis of claim 1, wherein the means for laterally retaining comprises at least one lateral projection structure extending outwardly from at least one side of the at least one projection structure.

3. The implantable orthopedic prosthesis of claim 1, wherein the means for laterally retaining comprises at least one retention aperture defined in the at least one projection structure and a corresponding cross pin adapted to mate with the at least one retention aperture.

4. The implantable orthopedic prosthesis of claim 3, wherein the corresponding cross pin is tapered along substantially all of a length of the cross pin in a direction of insertion into the at least one retention aperture.

5. The implantable orthopedic prosthesis of claim 4, wherein the at least one retention aperture is not tapered.

6. The implantable orthopedic prosthesis of claim 3, wherein the at least one retention aperture is tapered in a direction of insertion of the corresponding cross pin.

7. The implantable orthopedic prosthesis of claim 3, wherein the projection structure is a fin structure.

8. The implantable orthopedic prosthesis of claim 7, wherein the means for laterally retaining comprises at least two retention apertures defined in the fin structure and a corresponding cross pin adapted to mate with each retention aperture.

9. The implantable orthopedic prosthesis of claim 1, wherein the means for laterally retaining comprises at least one retention aperture defined in the at least one projection structure and a corresponding at least partially hollow cross pin into which a filler material is inserted, the cross pin having at least one radial aperture through which the filler material can flow.

10. The implantable orthopedic prosthesis of claim 1, wherein the projection structure is a structure selected from the set comprising: a generally linear peg, a non-linear peg, a generally planar fin, and a non-planar fin.

11. The implantable orthopedic prosthesis of claim 1, wherein the projection structure is comprised of a porous metal capable of lateral fluid communication between generally opposing sides of the projection structure to permit tissue in growth through the projection structure post operatively.

12. The implantable orthopedic prosthesis of claim 1, wherein a depth of the projection structure extends inwardly from the fixation surface of the implant body a distance at least as large as a cross-sectional depth of the implant body measured at a location other than a location of the projection structure.

13. An implantable orthopedic prosthesis for implantation on a bone during a knee arthroplasty procedure, the implantable prosthesis comprising:
    an implant body having a fixation surface for fixation to the bone and an articulation surface adapted to articulate with a second knee arthroplasty implant;
    at least one projection structure extending inwardly from the fixation surface of the implant body toward the bone; and
    a lateral retention structure extending laterally of the at least one projection structure such that, when the implant body fixation surface is fixated to the bone in an unloaded condition, as the lateral retention structure is advanced into a corresponding channel formed in the bone a preload force generated by the lateral retention structure oriented inwardly from the fixation surface towards the bone is exerted on the implant body biasing the fixation surface of the implant body against an outer surface of the bone and a compressive force is exerted between the corresponding channel and the lateral retention structure.

14. The implantable orthopedic prosthesis of claim 13, wherein lateral retention structure comprises at least one retention aperture defined in the at least one projection structure and a corresponding cross pin adapted to mate with the at least one retention aperture.

15. The implantable orthopedic prosthesis of claim 14, wherein one of the retention aperture and corresponding cross pin is tapered and the other is not tapered.

16. The implantable orthopedic prosthesis of claim 13, wherein the lateral retention structure comprises at least one retention aperture defined in the at least one projection structure and a corresponding at least partially hollow cross pin into which a filler material is inserted, the cross pin having at least one radial aperture through which the filler material can flow.

17. An implantable orthopedic prosthesis for implantation on a bone during a knee arthroplasty procedure, the implantable prosthesis comprising:
    an implant body having a fixation surface adapted to face and fixate to an outer surface of the bone and an articulation surface adapted to articulate with a second knee arthroplasty implant;
    at least one projection structure extending inwardly from the fixation surface of the implant body toward the bone; and a lateral retention structure extending laterally of the at least one projection structure such that, when the implant body fixation surface is fixated to the outer surface of the bone in an unloaded condition, as the lateral retention structure is advanced in a first direction into a corresponding channel formed in the bone a preload force generated by the lateral retention structure oriented in a second direction is exerted on the implant body biasing the fixation surface of the implant body against the outer surface of the bone and a compressive force is exerted between the corresponding channel and the lateral retention structure, wherein the second direction is generally perpendicular to the first direction.

18. The implantable orthopedic prosthesis of claim 17, wherein the lateral retention structure comprises at least one retention aperture defined in the at least one projection structure and a corresponding cross pin adapted to mate with the at least one retention aperture and one of the retention aperture and corresponding cross pin is tapered and the other is not tapered.

* * * * *